US009750857B2

(12) United States Patent
Tout et al.

(10) Patent No.: US 9,750,857 B2
(45) Date of Patent: *Sep. 5, 2017

(54) SYSTEMS AND METHODS FOR TREATING A TISSUE SITE WITH REDUCED PRESSURE INVOLVING A REDUCED-PRESSURE INTERFACE HAVING A MULTI-LUMEN CONDUIT FOR CONTACTING A MANIFOLD

(71) Applicant: KCI Licensing, Inc., San Antonio, TX (US)

(72) Inventors: Aidan Marcus Tout, Alderbury (GB); Christopher Brian Locke, Bournermouth (GB)

(73) Assignee: KCI Licensing, Inc., San Antonio, TX (US)

( * ) Notice: Subject to any disclaimer, the term of this patent is extended or adjusted under 35 U.S.C. 154(b) by 189 days.

This patent is subject to a terminal disclaimer.

(21) Appl. No.: 14/678,698

(22) Filed: Apr. 3, 2015

(65) Prior Publication Data

US 2015/0273123 A1    Oct. 1, 2015

Related U.S. Application Data

(63) Continuation of application No. 13/554,542, filed on Jul. 20, 2012, now Pat. No. 9,023,012.

(Continued)

(51) Int. Cl.
*A61F 13/00* (2006.01)
*A61M 1/00* (2006.01)
*A61M 25/00* (2006.01)

(52) U.S. Cl.
CPC ..... *A61M 1/0088* (2013.01); *A61F 13/00068* (2013.01); *A61M 1/00* (2013.01);
(Continued)

(58) Field of Classification Search
CPC ...... A61F 13/00068; A61F 2013/00174; A61F 2013/00536; A61F 2013/0054;
(Continued)

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

Notice of Rejection corresponding to JP2104-52219 dated May 17, 2016.

(Continued)

*Primary Examiner* — Tatyana Zalukaeva
*Assistant Examiner* — Benjamin Klein

(57) ABSTRACT

Systems and methods for a reduced-pressure interface for connecting a multi-lumen conduit to a distribution manifold. The interface includes a housing having a flange portion and a cavity wall portion. The cavity wall portion forms a cavity having a tissue-facing cavity opening. The interface further includes an attachment device, a conduit port, and a multi-lumen conduit. The attachment device is coupled to a tissue-facing side of the flange portion for coupling the housing to a sealing member. The conduit includes a distal end and a proximal whereby the distal end extends through a conduit aperture and past the cavity wall portion into the cavity. The conduit further includes a primary lumen and a plurality of sensing lumens. The primary lumen and the plurality of sensing lumens extend from the proximal end of (Continued)

the conduit to the distal end. The conduit is adapted to contact the distribution manifold.

15 Claims, 10 Drawing Sheets

Related U.S. Application Data

(60) Provisional application No. 61/511,840, filed on Jul. 26, 2011, provisional application No. 61/511,827, filed on Jul. 26, 2011.

(52) U.S. Cl.
CPC .......... *A61M 1/0025* (2014.02); *A61M 25/00* (2013.01); *A61F 2013/0054* (2013.01); *A61F 2013/00174* (2013.01); *A61F 2013/00536* (2013.01); *A61M 2205/3344* (2013.01)

(58) Field of Classification Search
CPC .................. A61M 1/00; A61M 1/0025; A61M 1/0088–1/0092; A61M 25/00; A61M 2205/3344; A61M 27/00–27/002
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 9,023,012 B2 * | 5/2015 | Tout .................. A61M 1/0088 604/543 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0064132 A1 * | 4/2004 | Boehringer .......... A61M 1/0011 604/543 |
| 2005/0085795 A1 * | 4/2005 | Lockwood .......... A61M 1/0084 604/543 |
| 2007/0066946 A1 * | 3/2007 | Haggstrom .......... A61M 1/0031 604/313 |
| 2009/0270820 A1 * | 10/2009 | Johnson ............... A61M 1/0088 604/290 |
| 2010/0137775 A1 * | 6/2010 | Hu ....................... A61M 1/0088 602/54 |
| 2011/0282309 A1 * | 11/2011 | Adie .................... A61M 1/0088 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2007030598 A2 | 3/2007 |
| WO | 2010068502 A1 | 6/2010 |
| WO | 2010094957 A1 | 8/2010 |
| WO | 2011087871 A2 | 7/2011 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, Jun. 1997.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; mailed Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

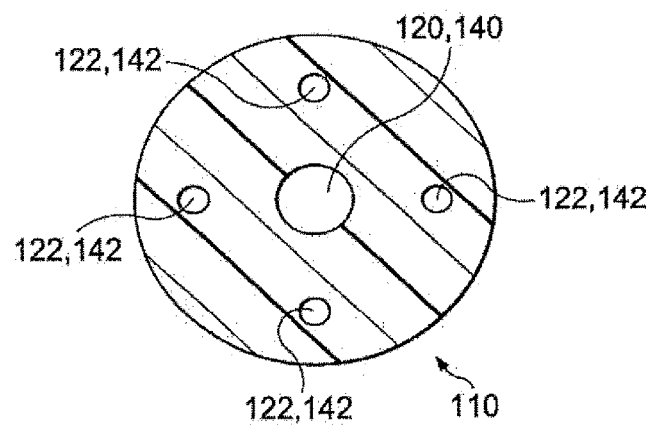
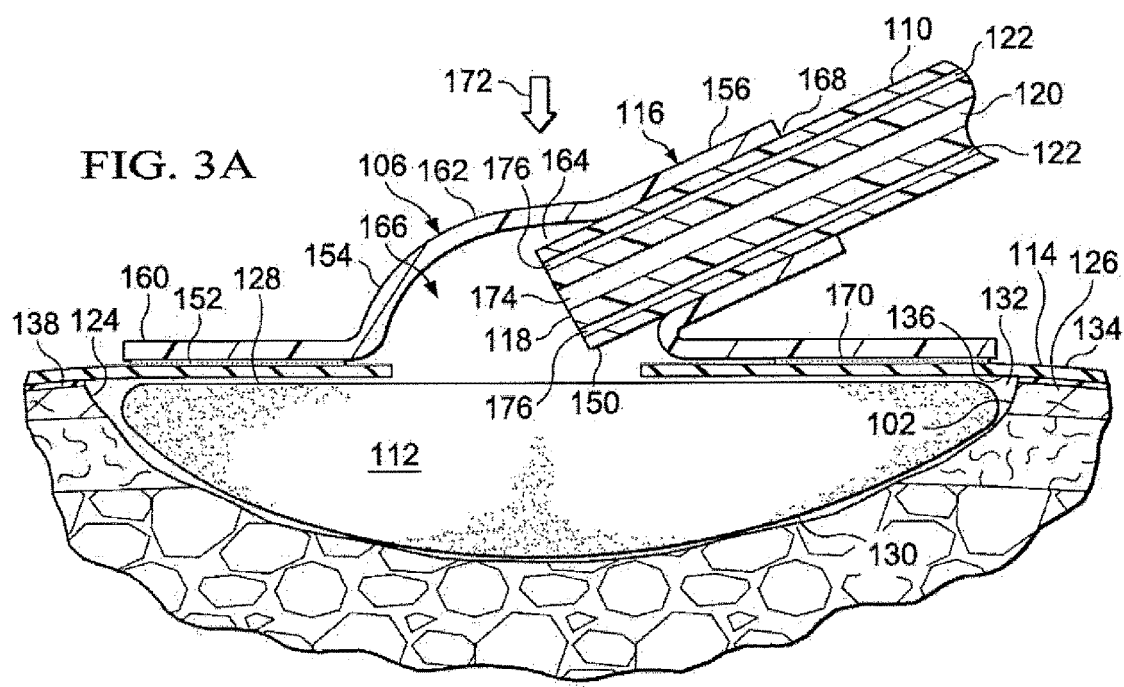

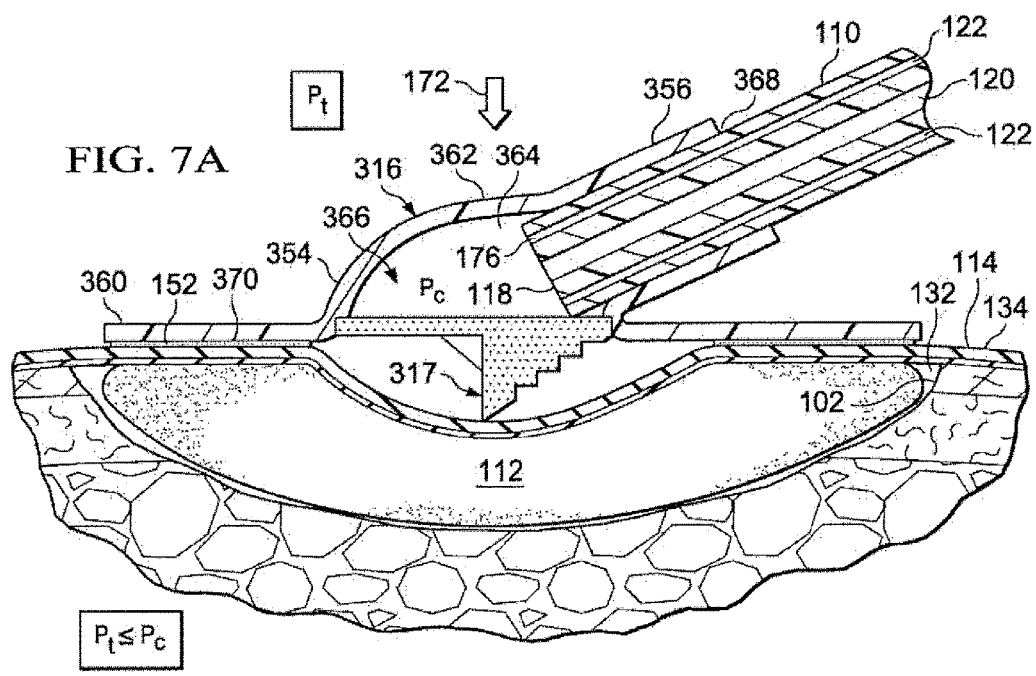
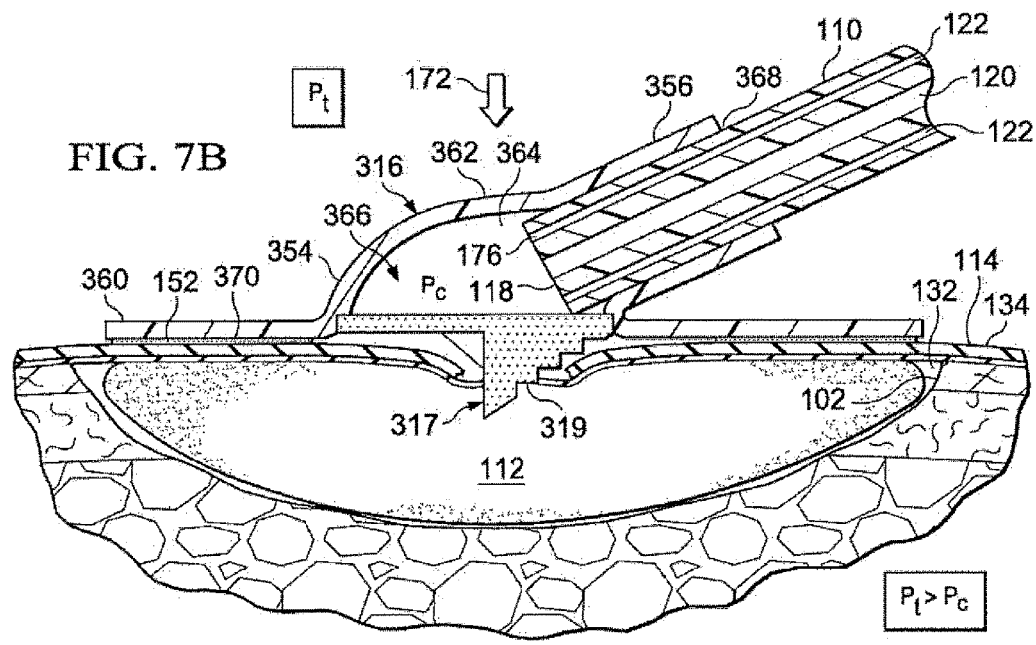

SYSTEMS AND METHODS FOR TREATING A TISSUE SITE WITH REDUCED PRESSURE INVOLVING A REDUCED-PRESSURE INTERFACE HAVING A MULTI-LUMEN CONDUIT FOR CONTACTING A MANIFOLD

RELATED APPLICATIONS

The present application is a continuation of U.S. patent application Ser. No. 13/554,542, entitled "Systems and Methods for Treating a Tissue Site with Reduced Pressure Involving a Reduced-Pressure Interface having a Multi-Lumen Conduit for Contacting a Manifold," filed Jul. 20, 2012, which claims the benefit, under 35 USC §119(c), of the filing of U.S. Provisional Patent Application Ser. No. 61/511,840, entitled "Systems and Methods for Treating a Tissue Site with Reduced Pressure Involving a Reduced-Pressure Interface having a Cutting Element," filed Jul. 26, 2011, and U.S. Provisional Patent Application Ser. No. 61/511,827, entitled "Systems and Methods for Treating a Tissue Site with Reduced Pressure Involving a Reduced-Pressure Interface having a Multi-Lumen Conduit for Contacting a Manifold," filed Jul. 26, 2011, which is incorporated herein by reference for all purposes.

BACKGROUND

The present disclosure relates generally to medical treatment systems and, more particularly, but not by way of limitation, to systems, methods, and apparatuses for treating a tissue site with reduced pressure involving a reduced-pressure interface having a multi-lumen conduit for contacting a manifold.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a manifold device, such as a porous pad. The porous pad contains cells or pores that distribute reduced pressure to the tissue and channel fluids that are drawn from the tissue.

SUMMARY

According to an illustrative embodiment a reduced-pressure interface for connecting a multi-lumen conduit to a distribution manifold is presented. The reduced-pressure interface includes a multi-lumen conduit that abuts, at least in part, a distribution manifold. The distribution manifold contacts at least some distal apertures that open into sensing lumens in the multi-lumen conduit. The distribution manifold may thereby protect those openings from liquids entering that might block the sensing lumens.

According to another illustrative embodiment, a system for treating a tissue site on a patient with reduced pressure includes a distribution manifold for placing proximate to the tissue site, a sealing member for covering the distribution manifold and a portion of intact epidermis of the patient to form a sealed space, a reduced-pressure interface for providing reduced pressure through the sealing member to the distribution manifold, a reduced-pressure source, and a multi-lumen conduit for fluidly coupling the reduced-pressure source to the reduced-pressure interface. The reduced-pressure interface includes a housing having a cavity wall portion. The cavity wall portion forms a cavity having a tissue-facing cavity opening. The reduced-pressure interface further includes an attachment device coupled to the housing for coupling the housing to the sealing member, a conduit port coupled to the cavity wall and having a conduit aperture, and a multi-lumen conduit. The multi-lumen conduit has a distal end and a proximal end. The distal end of the multi-lumen conduit extends through the conduit aperture into the cavity. The multi-lumen conduit further includes at least one primary lumen for delivering reduced pressure and a plurality of sensing lumens. The primary lumen and the plurality of sensing lumens extend from the distal end of the multi-lumen conduit towards the proximal end of the multi-lumen conduit. The plurality of sensing lumens have a corresponding plurality of distal openings at the distal end of the multi-lumen conduit. At least one of the plurality of distal openings of the plurality of sensing lumens contacts the distribution manifold.

The reduced-pressure interface allows the sensing lumens not to become blocked. This is because the distribution manifold is against at least one of the distal apertures and helps protect the sensing lumen from liquid entry. The reduced-pressure interface may also avoid spraying or an aerosol effect of liquids from the tissue site that might otherwise enter a sensing lumen.

According to another illustrative embodiment, a method for treating a tissue site on a patient with reduced pressure includes disposing a distribution manifold proximate to the tissue site and covering the distribution manifold and a portion of intact epidermis of the patient with a sealing member to form a sealed space in which the distribution manifold is disposed. The sealing member has a first side and a second, tissue-facing side. The method further includes providing a reduced-pressure source, providing a multi-lumen conduit having a distal end and a proximal end. The multi-lumen conduit includes a plurality of sensing lumens and at least one primary lumen. The method further includes fluidly coupling a distal end of the multi-lumen conduit to the sealed space and disposing at least one distal opening of a plurality of distal openings of the plurality of sensing lumens in contact with the distribution manifold. The method also includes delivering reduced pressure to the multi-lumen conduit.

According to another illustrative embodiment, a reduced-pressure connection for providing reduced pressure to a tissue site in a sealed space formed by a sealing member includes a distribution manifold for placing proximate to the tissue site and a multi-lumen conduit. The distribution manifold includes a foam member. The multi-lumen conduit has a plurality of sensing lumens and at least one primary lumen. A plurality of distal opening are associated with the plurality of sensing lumens on a distal end of the multi-lumen conduit. The distal end of the multi-lumen conduit is in direct contact with the distribution manifold such that at least one of the plurality of distal apertures abuts the distribution manifold.

According to another illustrative embodiment, a reduced pressure treatment system for treating a wound on a patient with reduced pressure includes a manifold for positioning adjacent to the wound, a drape for covering the manifold and a portion of intact epidermis of the patient to form a sealed space, a reduced-pressure interface for providing reduced pressure through the drape to the manifold, a reduced-pressure source, and a first conduit and a second conduit for fluidly coupling the reduced-pressure source to the reduced-pressure interface. The reduced-pressure interface includes a housing having a cavity wall portion that forms a cavity having a tissue-facing cavity opening, an attachment device coupled to the housing for coupling the housing to the drape, a conduit port coupled to the cavity wall and having a conduit aperture, and the first conduit and the second conduit. The first conduit and the second conduit have a distal end and a proximal end, such that the distal end extends through the conduit aperture into the cavity. The first conduit further includes at least one primary lumen for delivering reduced pressure such that the primary lumen extends from the distal end to the proximal end of the first conduit. The second conduit further includes a plurality of sensing lumens extending from the distal end to the proximal end of the second conduit. The plurality of sensing lumens have a corresponding plurality of distal openings at the distal end of the second conduit, and at least one of the plurality of distal openings of the plurality of sensing lumens contacts the manifold.

According to yet another illustrative embodiment, a method for treating a wound on a patient with reduced pressure includes positioning a manifold adjacent to the wound and covering the manifold and a portion of intact epidermis of the patient with a drape to form a sealed space. The drape has a first side and a second, tissue-facing side. The method further includes providing a reduced-pressure source and providing a first conduit and a second conduit. The first conduit and the second conduit have a distal end and a proximal end. The second conduit further includes a plurality of sensing lumens. The first conduit further includes at least one reduced-pressure lumen. The method further includes fluidly coupling the distal end of the first conduit and the second conduit to the drape, disposing at least one distal opening of a plurality of distal openings of the plurality of sensing lumens in contact with the manifold, and delivering reduced pressure to the first conduit.

According to another illustrative embodiment, a reduced-pressure connection for providing reduced pressure to a wound in a sealed space formed by a drape includes a manifold for placing proximate to the wound. The manifold includes a foam member. The connection further includes a first conduit having at least one primary lumen such that the first conduit has a distal end and a second conduit having a plurality of sensing lumens such that a plurality of distal opening are associated with the plurality of sensing lumens on a distal end of the second conduit. The distal end of the first and second conduits are in direct contact with the manifold such that at least one of the plurality of distal apertures abuts the manifold.

Other features and advantages of the illustrative embodiments will become apparent with reference to the drawings and detailed description that follow.

BRIEF DESCRIPTION OF THE DRAWINGS

FIG. 2 is a schematic, cross-sectional view of an illustrative embodiment of a multi-lumen conduit of the system shown in FIG. 1 taken along line 2-2;

FIG. 3A is a schematic, cross-sectional view of an illustrative embodiment of a reduced-pressure interface having a multi-lumen conduit extending into a cavity of the reduced-pressure interface;

FIG. 7A is a schematic, cross-sectional view of the reduced-pressure interface of FIG. 6 under reduced pressure but prior to the cutting element perforating a sealing member;

FIG. 7B is another schematic, cross-sectional view of the reduced-pressure interface of FIG. 6 under reduced pressure after the cutting member has perforated the sealing member;

DETAILED DESCRIPTION OF ILLUSTRATIVE EMBODIMENTS

Figure 1:
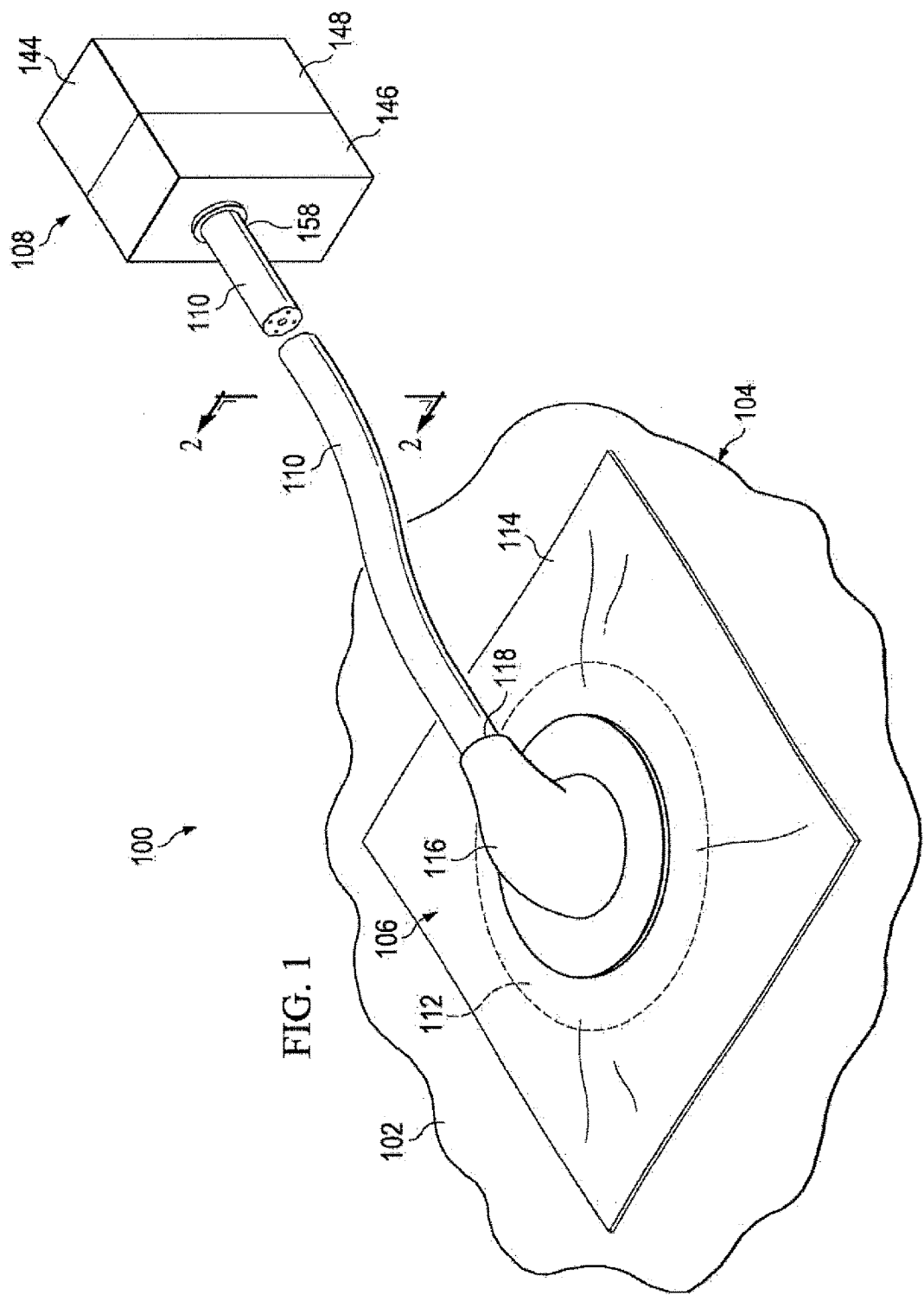
FIG. 1 is a schematic perspective view of an illustrative embodiment of a system for treating a tissue site with reduced pressure.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Unless otherwise indicated, quantitative values of pressure stated herein are gauge pressures. Reference to increases in reduced pressure typically refer to a decrease in absolute pressure, and decreases in reduced pressure typically refer to an increase in absolute pressure.

Referring now to the drawings and initially to FIGS. 1-3B, a system 100 for treating a tissue site 102 on a patient 104 with reduced pressure is presented. The system 100 includes a reduced-pressure dressing 106 for disposing proximate the tissue site 102. The system includes a reduced-pressure interface 116 that fluidly couples a multi-lumen conduit 110 to a distribution manifold 112. The reduced-pressure interface 116 may allow for an easily manufactured connection that allows at least one of a plurality of sensing lumens 122 within the multi-lumen conduit 110 to remain open or unblocked during operation. During operation, the sensing lumens 122 may remain unblocked by a distal end 118 of the multi-lumen conduit 110 being against (or abutting) or embedded in the distribution manifold 112 such that at least one distal aperture on the distal end 118 of the multi-lumen conduit 110 is in contact with the distribution manifold 112. This in turn avoids an open area where liquids may spray, foam, or otherwise travel towards the distal apertures and also offers a filter member in front of the distal apertures.

The system 100 also includes a reduced-pressure treatment unit 108 fluidly connected to the reduced-pressure dressing 106 through the multi-lumen conduit 110 for applying reduced pressure to the tissue site 102. The reduced-pressure dressing 106 further includes the distribution manifold 112, a sealing member 114, and the reduced-pressure interface 116. The reduced-pressure interface 116 is adapted to connect to the multi-lumen conduit 110. The multi-lumen conduit 110 has the distal end 118 and includes at least one primary lumen 120 and the sensing lumens 122. While usually there will be only one primary lumen 120, there could be additional larger lumens for transporting the reduced pressure to the tissue site 102 and concomitantly removing any fluids. The distal end 118 of the multi-lumen conduit 110 is adapted to extend into the reduced-pressure interface 116 and, at least partially, contact the distribution manifold 112. The multi-lumen conduit 110 may either abut or be embedded within the distribution manifold 112.

Extending the multi-lumen conduit 110 into the reduced-pressure interface 116 to promote contact between the distal end 118 of the multi-lumen conduit 110 and the distribution manifold 112 may, in addition to those previously mentioned, provide a number of benefits. The benefits may include ease of application, reduction of error when forming a seal between the multi-lumen conduit 110 and the distribution manifold 112, and reduction in instances of sensing lumen occlusion when fluid is removed from the tissue site 102. Instances where the sensing lumens 122 become occluded may disconnect the system's 100 ability to monitor levels of reduced pressure, and thus, control the reduced pressure at the tissue site 102.

Fluid removed from the tissue site 102 will follow the path of least resistance which preferentially is the primary lumen 120. When the primary lumen 120 and at least one of the sensing lumens 122 are not in direct contact with the manifold, the fluid may splash, foam, or otherwise fail to smoothly transition into the primary lumen 120. When the fluid splashes or foams, the fluid may enter the sensing lumens 122 occluding the sensing lumens 122. Should all of the sensing lumens 122 become occluded, the sensing lumens 122 are effectively disabled from sensing the reduced pressure levels at the tissue site 102. When the primary lumen 120 and at least one of the sensing lumens 122 are in contact with the distribution manifold 112, the fluid withdrawn from the tissue site 102 tends to bypass entering the sensing lumens 122 contacting the distribution manifold 112 and flow into the primary lumen 120. The distribution manifold 112 may further provide a barrier between the primary lumen 120 and the at least one of the plurality of sensing lumens 122 contacting the distribution manifold 112. Additionally, having the multi-lumen conduit 110 in direct contact with the distribution manifold 112 may help ensure that there is a constant low velocity liquid flow into the multi-lumen conduit 110 which may minimize the instance of aerosolized particles being deposited around the at least one sensing lumen 122 contacting the distribution manifold 112 and may also provide a filter to liquids entering the at least one sensing lumen 122.

In prior reduced pressure treatment systems using a reduced pressure interface and a multi-lumen conduit, the reduced pressure interfaces have been designed to remove the sensory lumens from direct contact with the distribution manifold to inhibit fluid from occluding the sensory lumens. However, testing has shown that removing the sensory lumens from contacting the distribution manifold creates splashing and foaming that may occlude the sensory lumens undermining the purpose of removing the sensory lumens from contacting the distribution manifold.

The system 100 may be used with various different types of tissue sites 102. The tissue site 102 may be a wound 124 or wound cavity. As shown in at least FIGS. 3A-3B, the tissue site 102 or the wound 124, may be through an epidermis 126 and into a subcutaneous tissue or any other tissue. The tissue site 102 may be the bodily tissue of any human, animal, or other organism, including bone tissue, adipose tissue, muscle tissue, dermal tissue, vascular tissue, connective tissue, cartilage, tendons, ligaments, body cavity or any other tissue. Treatment of the tissue site 102 may include removal of fluids, e.g., exudate or ascites.

Referring still to FIGS. 1-3B, the distribution manifold 112 is proximate the tissue site 102 and has a first side 128 and a second, tissue-facing side 130. The term "distribution manifold" as used herein generally refers to a substance or structure that is provided to assist in applying reduced pressure to, delivering fluids to, or removing fluids from the tissue site 102. The distribution manifold 112 typically includes a plurality of flow channels or pathways that distribute fluids provided to and removed from the tissue site 102 around the distribution manifold 112. In one illustrative embodiment, the flow channels or pathways are interconnected to improve distribution of fluids provided or removed from the tissue site 102. The distribution manifold 112 may be a biocompatible material that is capable of being placed in contact with the tissue site 102 and distributing reduced pressure to the tissue site 102. Examples of the distribution manifold 112 may include, without limitation, devices that have structural elements arranged to form flow channels, such as, for example, cellular foam, open-cell foam, porous tissue collections, liquids, gels, and foams that include, or cure to include, flow channels. The distribution manifold 112 may be porous and may be made from foam, gauze, felted mat, or any other material suited to a particular biological application. In one embodiment, the distribution manifold 112 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the distribution manifold 112 may also be used to distribute fluids such as medications, antibacterials, growth factors, and various solutions to the tissue site 102. Other layers may be included in or on the distribution manifold 112, such as absorptive materials, wicking materials, hydrophobic materials, and hydrophilic materials.

In one illustrative embodiment, the distribution manifold 112 may be constructed from bioresorbable materials that do not have to be removed from a patient's body following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 112 may further serve as a scaffold for new cell-growth, or a scaffold material may be used in conjunction with the distribution manifold 112 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The distribution manifold 112 may be covered by the sealing member 114, which may also be referred to as a drape. The sealing member 114 forms a sealed space 132 over the tissue site 102. The sealing member 114 has a first side 134, and a second, tissue-facing side 136. The sealing member 114 may be any material that provides a fluid seal. "Fluid seal," or "seal," means a seal adequate to maintain reduced pressure at a desired site given the particular reduced-pressure source or subsystem involved. The sealing member 114 may, for example, be an impermeable or semi-permeable, elastomeric material. "Elastomeric" means having the properties of an elastomer. Elastomer generally refers to a polymeric material that has rubber-like properties. More specifically, most elastomers have ultimate elongations greater than 100% and a significant amount of resilience. The resilience of a material refers to the material's ability to recover from an elastic deformation. Elastomers that are relatively less resilient may also be used as these elastomers are more likely to tear when faced with the cutting element. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of dressing sealing member materials include a silicone drape, 3M Tegaderm® drape, polyurethane (PU) drape such as one available from Avery Dennison Corporation of Pasadena, Calif. An additional, specific non-limiting example of a dressing sealing member material includes a 30 µm matt polyurethane film such as the Inspire™ 2317 manufactured by Exopack™ Advanced Coatings of Matthews, N.C. The sealing member 114 may be preformed with an aperture or other means to transmit fluid from the distribution manifold to the reduced-pressure treatment unit 108. Alternatively, a healthcare provider may cut the sealing member to form an aperture or a cutting element attached to a reduced-pressure interface may be used to form an aperture.

An attachment device 138 may be used to hold the sealing member 114 against a portion of the patient's intact epidermis 126 or another layer, such as a gasket or additional sealing member. The attachment device 138 may take numerous forms. For example, the attachment device 138 may be a medically acceptable adhesive, such as a pressure-sensitive adhesive, that extends about a periphery or all of the sealing member 114. The attachment device 138 may also be a sealing ring or other device. The attachment device 138 is disposed on the second, tissue-facing side 136 of the sealing member 114. Before use, the attachment device 138 may be covered by a release liner (not shown).

The reduced-pressure interface 116 may be positioned adjacent to or coupled to the sealing member 114 to provide fluid access to the distribution manifold 112. Another attachment device 152 similar to the attachment device 138 may be used to hold the reduced-pressure interface 116 against the sealing member 114. The multi-lumen conduit 110 fluidly couples the reduced-pressure treatment unit 108 and the reduced-pressure interface 116. The reduced-pressure interface 116 allows the reduced pressure to be delivered to the tissue site 102. While the amount and nature of reduced pressure applied to a tissue site will typically vary according to the application, the reduced pressure will typically be between −5 min Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

As shown, the multi-lumen conduit 110 includes the primary lumen 120 and the plurality of sensing lumens 122. In one illustrative embodiment, the primary lumen 120 is a central lumen 140 and the plurality of sensing lumens 122 are peripheral lumens 142. The primary lumen 120 and the plurality of sensing lumens 122 are adapted to maintain fluid isolation between the primary lumen 120 and the plurality of sensing lumens 122 as the multi-lumen conduit 110 transports fluids from the reduced-pressure interface 116 to the reduced-pressure treatment unit 108. Liquids or exudates communicated from the distribution manifold 112 through the primary lumen 120 are removed from the multi-lumen conduit 110 and retained within a liquid-collection chamber (not explicitly shown) in fluid communication with the reduced-pressure treatment unit 108. The plurality of sensing lumens 122 fluidly communicates reduced pressure representative of the tissue site 102 to an instrumentation unit 144.

The reduced-pressure treatment unit 108 may include a liquid-collection chamber, or a collection canister, and the instrumentation unit 144 in fluid communication with a reduced-pressure source 146. The instrumentation unit 144 may include a microprocessor 148 adapted to process pressure signals received by the multi-lumen conduit 110, monitor the pressure signals, and issue alerts according to a pre-determined pressure configuration.

In an illustrative embodiment, the reduced-pressure source 146 is an electrically-driven vacuum pump. In another implementation, the reduced-pressure source 146 may instead be a manually-actuated or manually-charged pump that does not require electrical power. The reduced-pressure source 146 instead may be any other type of reduced pressure pump, or alternatively a wall suction port such as those available in hospitals and other medical facilities. The reduced-pressure source 146 may be housed within or used in conjunction with the reduced-pressure treatment unit 108, which may also include the instrumentation unit 144. The instrumentation unit 144 may include sensors, processing units, alarm indicators, memory, databases, software, display units, and user interfaces that further facilitate the application of reduced pressure treatment to the tissue site 102.

In one example, pressure-detection sensors (not shown) located in the instrumentation unit 144 may be disposed at or near the reduced-pressure source 146. The pressure-detection sensors may receive pressure data, or a pressure signal, from the reduced-pressure interface 116 via at least one of the plurality of sensing lumens 122 that is dedicated to delivering reduced pressure data to the pressure-detection sensors. The pressure signal or data may be representative of a pressure at a distal end 150 of any one of the plurality of sensing lumens 122. The pressure-detection sensors may communicate with a processing unit that monitors and controls the reduced pressure that is delivered by the reduced-pressure source 146.

Figure 3B:
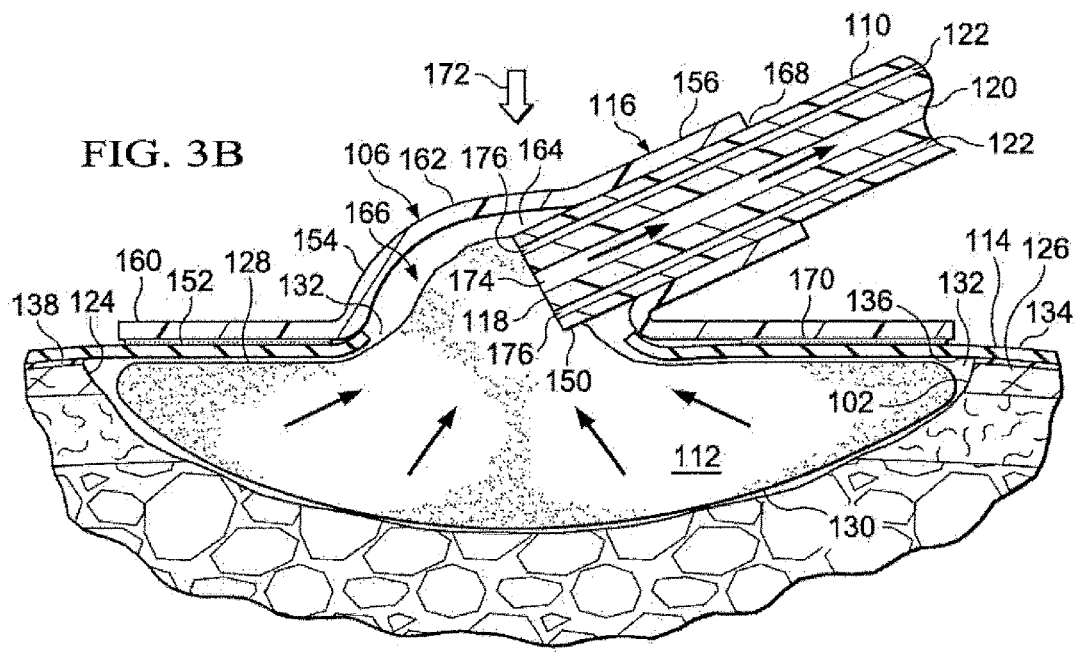
FIG. 3B is a schematic, cross-sectional view of the reduced-pressure interface of FIG. 3A under reduced pressure with a distribution manifold contacting the multi-lumen conduit.

Referring now primarily to FIG. 3A-3B, an illustrative embodiment of the reduced pressure interface 116 is presented in more detail. The reduced-pressure interface 116 includes a housing 154, a conduit port 156 coupled to the housing 154, the attachment device 152 for coupling the reduced-pressure interface 116 to the sealing member 114, and the multi-lumen conduit 110.

The housing 154 may have a flange portion 160 and a cavity wall portion 162. The cavity wall portion 162 forms a cavity 164 having a tissue-facing cavity opening 166. The conduit port 156 is coupled to or formed as part of the cavity wall portion 162 of the housing 154. The conduit port 156 includes a conduit aperture 168 whereby the conduit port 156 is adapted to receive the multi-lumen conduit 110. The attachment device 152 may be coupled to a tissue-facing side 170 of the flange portion 160 for coupling the housing 154 to the first side 134 of the sealing member 114. The housing 154 is made of a semi-rigid material that is capable of collapsing under a force such as a driving force 172. In a non-limiting example, the reduced-pressure interface 116, and thus the housing 154, may be made from a plasticized polyvinyl chloride (PVC), polyurethane, cyclic olefin copolymer elastomer, thermoplastic elastomer, poly acrylic, silicone polymer, and polyether block amide copolymer.

The multi-lumen conduit 110 includes the distal end 118 and a proximal end 158. The distal end 118 extends through the conduit aperture 168 and past the cavity wall portion 162 into the cavity 164. In one specific, non-limiting embodiment, the distal end 118 extends past the cavity wall portion 162 up to 5 mm. It should be understood, however, that the distal end 1118 may extend past the cavity wall portion 162 beyond 5 mm. The extent to which the distal end 118 extends past the cavity wall portion 162 may be determined based on the housing's 154 ability to collapse under the driving force 172. The proximal end 158 of the multi-lumen conduit 110 connects to the reduced-pressure treatment unit 108. In one embodiment, the multi-lumen conduit 110 is connected to the conduit port 156. The multi-lumen conduit 110 may be connected to the conduit port 156 by a weld or adhesive. While the multi-lumen conduit 110 is shown as extending past the cavity wall portion 162, the multi-lumen conduit 110 may be flush with the cavity wall portion 162 (not shown). The multi-lumen conduit 110 is adapted for at least a portion of the distal end 118 of the multi-lumen conduit 110 to contact the distribution manifold 112 during reduced pressure therapy. In one embodiment, a distal aperture 174 of the primary lumen 120 and a distal aperture 176 of at least one of the plurality of sensing lumens 122 is adapted to contact the distribution manifold 112.

In operation, a method for treating the tissue site 102 on the patient 104 with reduced pressure includes disposing the distribution manifold 112 proximate to the tissue site 102. The distribution manifold 112 and the portion of intact epidermis 126 of the patient 104 is covered with the sealing member 114 to form the sealed space 132 in which the distribution manifold 112 is disposed. The sealing member 114 has the first side 134 and the second, tissue-facing side 136. The reduced-pressure interface 116 is coupled proximate the first side 134 of the sealing member 114. The multi-lumen conduit 110 couples the reduced-pressure interface 116 to the reduced-pressure source 146. The reduced-pressure interface 116 includes the housing 154 having the flange portion 160 and the cavity wall portion 162, such that the cavity wall portion 162 forms the cavity 164 having the tissue-facing cavity opening 166. The attachment device 138 coupled to the tissue-facing side 170 of the flange portion 160 of the housing 154 connects the housing 154 to the sealing member 114. The reduced-pressure interface 116 further includes the conduit port 156 coupled to the cavity wall portion 162 having the conduit aperture 168 for receiving and coupling to the multi-lumen conduit 110. The multi-lumen conduit 110 includes the distal end 118 and the proximal end 158. The distal end 118 extends through the conduit aperture 168 and past the cavity wall portion 162 into the cavity 164. The multi-lumen conduit 110 further includes the primary lumen 120 for delivering reduced pressure and the plurality of sensing lumens 122. The primary lumen 120 and the plurality of sensing lumens 122 extend from the proximal end 158 of the multi-lumen conduit 110 to the distal end 118. At least a portion of the distal end 118 of the multi-lumen conduit 110 is positioned in contact with the distribution manifold 112.

The multi-lumen conduit 110 is connected to the conduit port 156. In one embodiment, the multi-lumen conduit 110 is welded to the conduit port 156 prior to packaging. In another embodiment, the multi-lumen conduit 110 is attached to the conduit port 156 by an adhesive.

An aperture is formed in the sealing member 114 for providing fluid communication between the housing 154 and the distribution manifold 112. The aperture may be preformed, formed by a healthcare provider, or formed by a cutting element on the reduced-pressure interface 116.

The step of coupling the reduced-pressure interface 116 proximate to the first side 134 of the sealing member 114 may include using the attachment device 152 of the reduced-pressure interface 116 to adhere the reduced-pressure interface 116 to the sealing member 114.

The step of positioning at least a portion of the distal end 118 of the multi-lumen conduit 110 in contact with the distribution manifold 112 may further include positioning the distal aperture 174 of the primary lumen 120 and the distal aperture 176 of at least one of the plurality of sensing lumens 122 in contact with the distribution manifold 112. In one embodiment, the distal aperture 176 of the at least one of the plurality of sensing lumens 122 is positioned below the distal aperture 174 of the primary lumen 120 relative to the distribution manifold 112.

In another embodiment, the step of positioning the at least the portion of the distal end 118 of the multi-lumen conduit 110 in contact with the distribution manifold 112 further includes applying the driving force 172 to the reduced-pressure interface 116 of sufficient strength to cause the at least the portion of the distal end 118 of the multi-lumen conduit 110 to contact the distribution manifold 112. The driving force 172 may push the multi-lumen conduit 110 into the distribution manifold 112. In one embodiment the driving force 172 may pull the distribution manifold 112 into the multi-lumen conduit 110. In yet another embodiment, the driving force 172 may both push the multi-lumen conduit 110 into the distribution manifold 112 while pulling the distribution manifold 112 into the multi-lumen conduit 110.

The step of positioning the at least the portion of the distal end 118 of the multi-lumen conduit 110 in contact with the distribution manifold 112 may further comprise applying a reduced pressure.

In one embodiment, the step of positioning the at least the portion of the distal end 118 of the multi-lumen conduit 110 in contact with the distribution manifold 112 further comprises applying reduced pressure through the reduced-pressure interface 116 to create sufficient reduced pressure in the cavity 164 to pull a portion of the distribution manifold 112 into the cavity 164 such that the distribution manifold 112 abuts the distal aperture 174 of the primary lumen 120.

In another embodiment, the step of positioning the at least the portion of the distal end 118 of the multi-lumen conduit 110 in contact with the distribution manifold 112 further comprises the step of applying reduced pressure through the reduced-pressure interface 116 to create sufficient reduced pressure in the cavity 164 to push the housing 154 towards the distribution manifold 112 such that the distal aperture 174 of the primary lumen 120 and the distal aperture 176 of the at least one of the sensory lumens 122 abuts the distribution manifold 112.

In yet another embodiment, the step of positioning the at least the portion of the distal end 118 of the multi-lumen conduit 110 in contact with the distribution manifold 112 further comprises manually applying the driving force 172 to an exterior of the reduced-pressure interface 116.

In one embodiment, the step of applying the driving force 172 to the reduced-pressure interface 116 comprising applying reduced pressure to the cavity 164 less than the threshold pressure ($P_t$) such that the wall portion collapses driving the multi-lumen conduit 110 into the distribution manifold 112.

Figure 4:
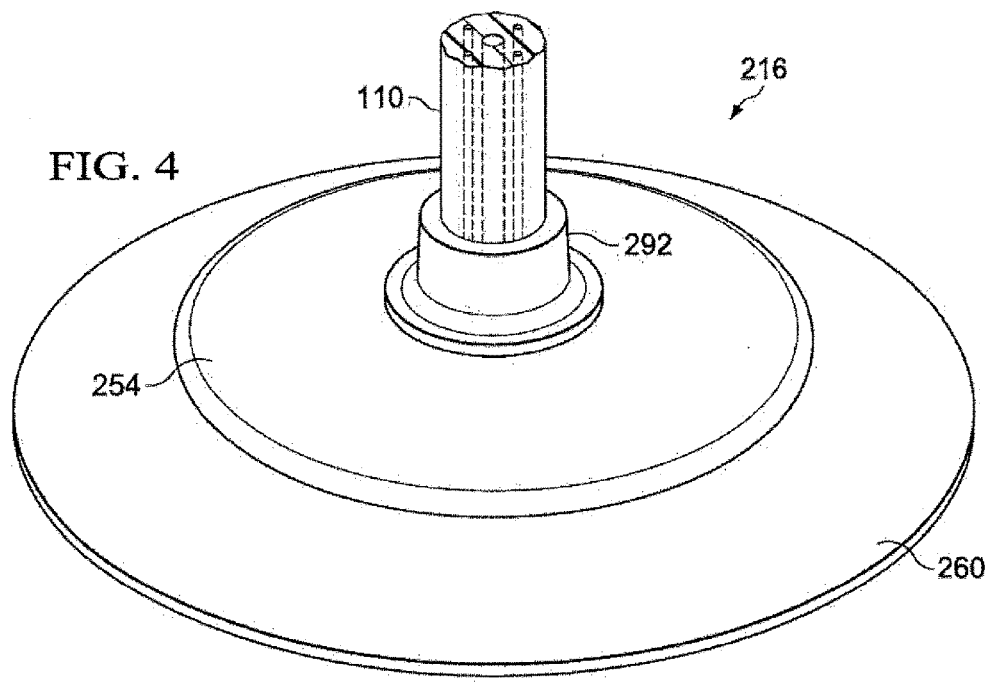
FIG. 4 is a schematic, top perspective view of another illustrative embodiment of a reduced-pressure interface having a multi-lumen conduit extending into a cavity of the reduced-pressure interface.
Figure 5A:
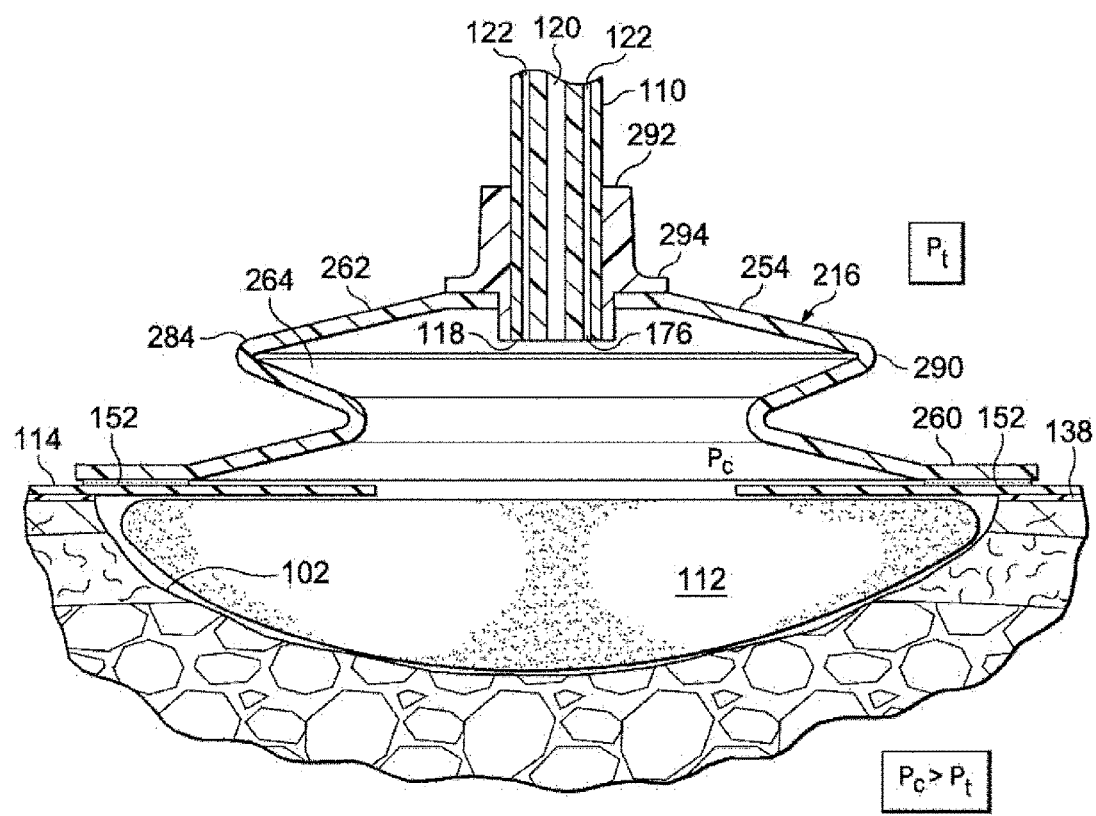
FIG. 5A is a schematic, cross-sectional view of the reduced-pressure interface of FIG. 4 as applied to a tissue site.
Figure 5B:
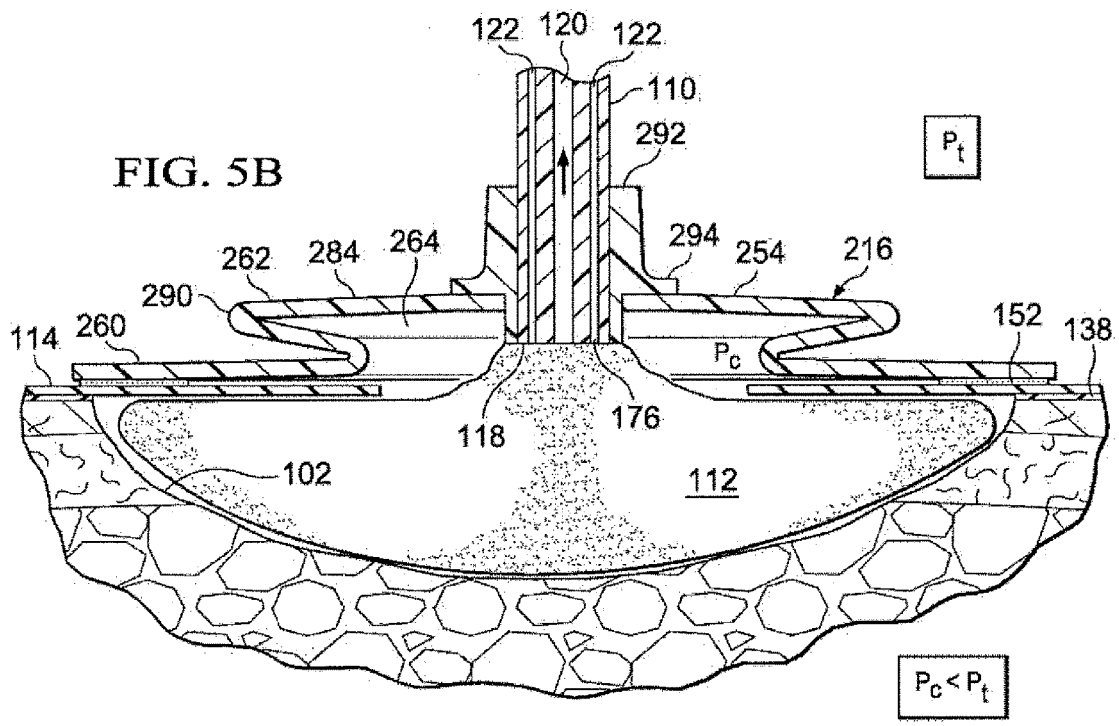
FIG. 5B is a schematic, cross-sectional view of the reduced-pressure interface of FIG. 5A under reduced pressure such that the distribution manifold contacts the multi-lumen conduit.

Referring now primarily to FIGS. 4-5B, another illustrative embodiment of a reduced-pressure interface 216 is presented. The reduced-pressure interface 216 is analogous in many respects to the reduced-pressure interface of FIGS. 3A-3B. The reduced-pressure interface 216 includes a housing 254 that may have a flange portion 260 and a cavity wall portion 262. The flange portion 260 may be coupled to the sealing member 114 by the attachment device 152. The cavity wall portion 262 is collapsible under reduced pressure. In one embodiment, the cavity wall portion 262 is collapsible under manual pressure. The cavity wall portion 262 may include a bellows configuration 290 for permitting the cavity wall portion 262 to collapse when a cavity 264 pressure ($P_c$) inside the cavity 264 is less than a threshold pressure ($P_t$) on an absolute pressure side.

The reduced-pressure interface 216 may further include a conduit adapter 292 for receiving the multi-lumen conduit 110 to provide fluid communication between the reduced-pressure treatment unit 108 and the tissue site 102. The conduit adapter 292 includes an adapter flange 294. The adapter flange 294 is positioned on an exterior 284 of the cavity wall portion 262. In a specific, non-limiting example, the conduit adapter 292 and the adapter flange 294 may be formed from materials to include plasticized polyvinyl chloride (PVC), polyurethane, cyclic olefin copolymer elastomer, thermoplastic elastomer, poly acrylic, silicone polymer, and polyether block amide copolymer.

The multi-lumen conduit 110 is connected to the conduit adapter 292. In a specific, non-limiting embodiment, the multi-lumen conduit 110 may be connected to the conduit adapter 292 by a weld or an adhesive. The multi-lumen conduit 110 extends beyond the conduit adapter 292 into the cavity 264. The reduced-pressure interface 216 is configured to position the distal end 118 of the multi-lumen conduit 110 in contact with the distribution manifold 112.

In one embodiment, reduced pressure applied through the reduced-pressure interface 216 may create sufficient reduced pressure in the cavity 264 to pull a portion of the distribution manifold 112 into the cavity 264 and abut the primary lumen 120 of the multi-lumen conduit 110. In another embodiment, the distribution manifold 112 may be partially pulled into the primary lumen 120. The distribution manifold 112 abuts the distal end 118 of the multi-lumen conduit 110 including the distal aperture 176 of the at least one of the plurality of sensing lumens 122. Allowing the distribution manifold 112 to completely abut the distal end 118 of the multi-lumen conduit 110 may help ensure fluid isolation between each of the lumens in the multi-lumen conduit 110.

Figure 6:
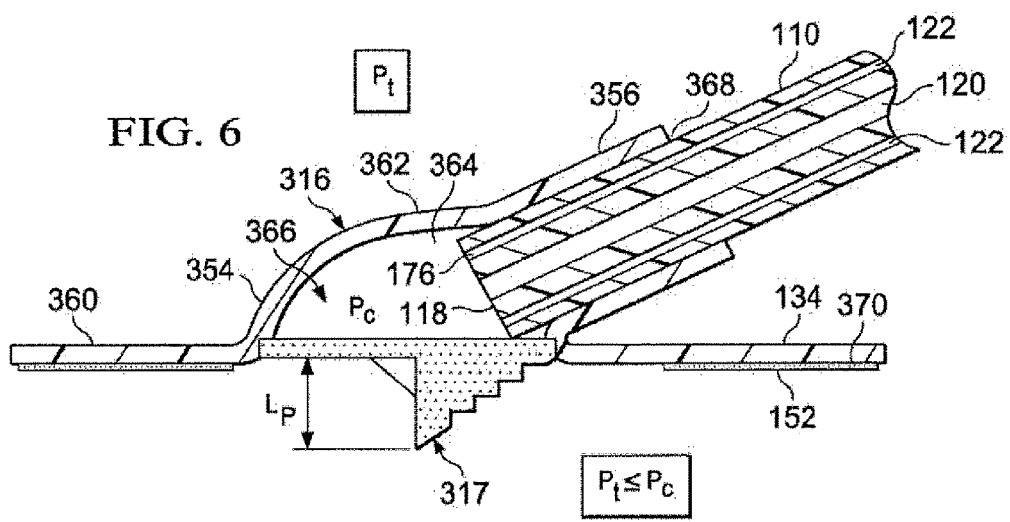
FIG. 6 is a schematic, cross-sectional view of one illustrative embodiment of a reduced-pressure interface having a cutting element for use as part of a system for treating a tissue site with reduced pressure.
Figure 7C:
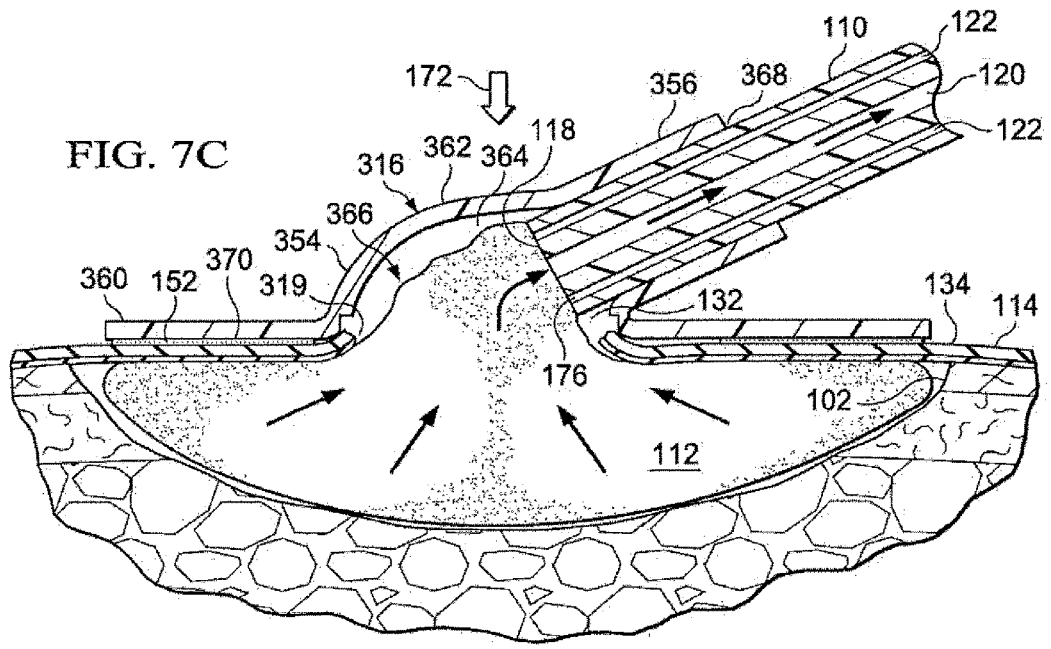
FIG. 7C is another schematic, cross-sectional view of the reduced-pressure interface of FIG. 6 under reduced pressure after the cutting member has perforated the sealing member and the cutting element has been removed.

Referring now primarily to FIGS. 6-7C, another illustrative embodiment of a reduced-pressure interface 316 is presented. The reduced-pressure interface 316 is analogous in many respects to the reduced-pressure interface of FIGS. 3A-3B. The reduced-pressure interface 316 includes a housing 354, a conduit port 356 coupled to the housing 354, and the attachment device 152 for coupling the reduced-pressure interface 316 to the sealing member 114. The reduced-pressure interface 316 further includes a cutting element 317.

The housing 354 may have a flange portion 360 and a cavity wall portion 362. The cavity wall portion 362 forms a cavity 364 having a tissue-facing cavity opening 366. The conduit port 356 is coupled to or formed as part of the cavity wall portion 362 of the housing 354. The conduit port 356 includes a conduit aperture 368 whereby the conduit port 356 is adapted to receive the multi-lumen conduit 110. The attachment device 152 may be coupled to a tissue-facing side 370 of the flange portion 360 for coupling the housing 354 to the first side 134 of the sealing member 114. The housing 354 is made of a semi-rigid material that is capable of collapsing under a force such as the driving force 172. In a non-limiting example, the reduced-pressure interface 316, and thus the housing 354, may be made from a plasticized polyvinyl chloride (PVC), polyurethane, cyclic olefin copolymer elastomer, thermoplastic elastomer, poly acrylic, silicone polymer, and polyether block amide copolymer.

The cutting element 317 may be at least temporarily coupled to the housing 354 proximate to the tissue-facing cavity opening 366. The cutting element 317 is adapted to form an aperture 319 in the sealing member 114 when the cutting element 317 is driven into the sealing member 114 with the driving force 172. The driving force 172 may also cause the cutting element 317 to penetrate or cut a portion of the distribution manifold 112.

The cutting element 317 may have a piercing length ($L_p$). The distribution manifold 112 may have a thickness greater than T when subject to reduced pressure such that the piercing length ($L_p$) of the cutting element 317 is less than the thickness T, i.e., $L_p < T$. One benefit of the piercing length ($L_p$) being less than the thickness, T, of the distribution manifold 112 under reduced pressure is that the cutting element 317 cannot completely cut through the distribution manifold 112 and reach the tissue site 102.

As previously mentioned, the cutting element 317 may be only temporarily coupled to the housing 354. In one embodiment, the cutting element 317 may be removed by a care giver. In another embodiment, the cutting element 317 may be formed from a liquid soluble material such as a water soluble material adapted to allow the cutting element 317 to dissolve. For example, the water soluble material may include at least one of the following: Polyvinyl alcohol (PVOH), polyvinyl pyrrolidone, hydroxyl and carboxyl modified cellulose, hydroxyl and carboxyl modified acrylics, starch, sugars (sucrose, glucose, fructose), weak acids (tartaric, citric, malic), salts (sodium chloride, sodium carbonate, sodium bicarbonate), polyethylene oxide (PEO), polyethylene glycol (PEG). The cutting element 317 may dissolve as liquids are removed from the tissue site 102. Reduced pressure is applied to the reduced-pressure interface 316 after perforating the sealing member 114 typically causing liquids to be removed from the tissue site 102. After a sufficient amount of time, liquids removed from the tissue site 102 cause the cutting element 317 to substantially dissolve. The cutting element 317 may dissolve within 2 minutes, 5 minutes, 10 minutes, or another time period. As the cutting element 317 is dissolved the cutting element 317 is removed by the multi-lumen conduit 110 with liquids from the tissue site 102. A liquid, e.g., saline solution, may also be introduced through the multi-lumen conduit 110, or otherwise, to dissolve the cutting element 317.

As shown in FIG. 7C, once the cutting element 317 has substantially dissolved, reduced pressure applied through the reduced-pressure interface 316 creates sufficient reduced pressure in the cavity 364 to pull a portion of the distribution manifold 112 into the cavity 364 such that the distribution manifold 112 abuts a distal end 118 of the multi-lumen conduit 110 to include the distal aperture 176 of the at least one of the plurality of sensing lumens 122. Allowing the distribution manifold 112 to completely abut the distal end 118 of the multi-lumen conduit 110 may help ensure fluid isolation between each of the lumens in the multi-lumen conduit 110.

In operation, a caregiver may treat the tissue site 102 on the patient 104 with a method that includes disposing the distribution manifold 112 proximate to the tissue site 102. The distribution manifold 112 and the portion of intact epidermis 126 of the patient 104 is covered with the sealing member 114 to form the sealed space 132 in which the distribution manifold 112 is disposed. The reduced-pressure interface 316 is coupled to the sealing member 114. The multi-lumen conduit 110 is fluidly coupled on one end to the reduced-pressure source 146 and on the opposing end to the reduced-pressure interface 316. The driving force 172 is then applied to the reduced-pressure interface 316 with sufficient strength to cause the cutting element 317 to perforate (e.g., pierce, tear, cut or otherwise create the aperture 319) the sealing member 114.

Figure 8:
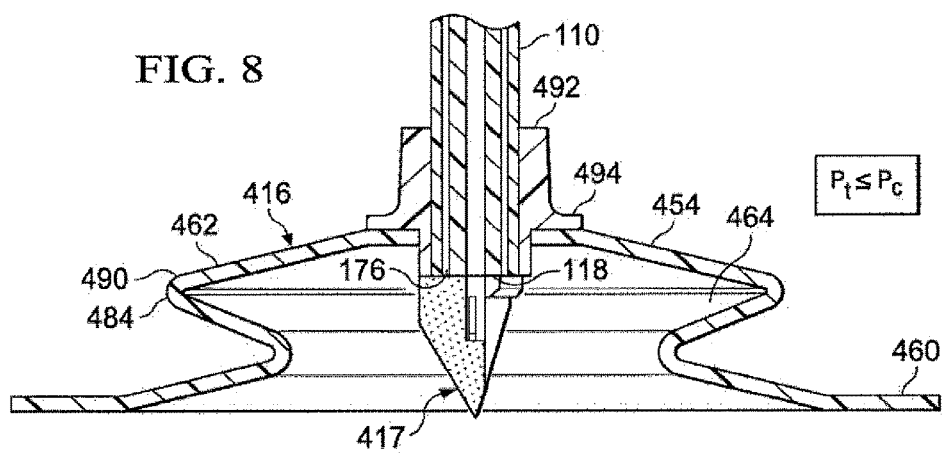
FIG. 8 is a schematic, cross-sectional view of another illustrative embodiment of a reduced-pressure interface having a cutting element for use as part of a system for treating a tissue site with reduced pressure.
Figure 9A:
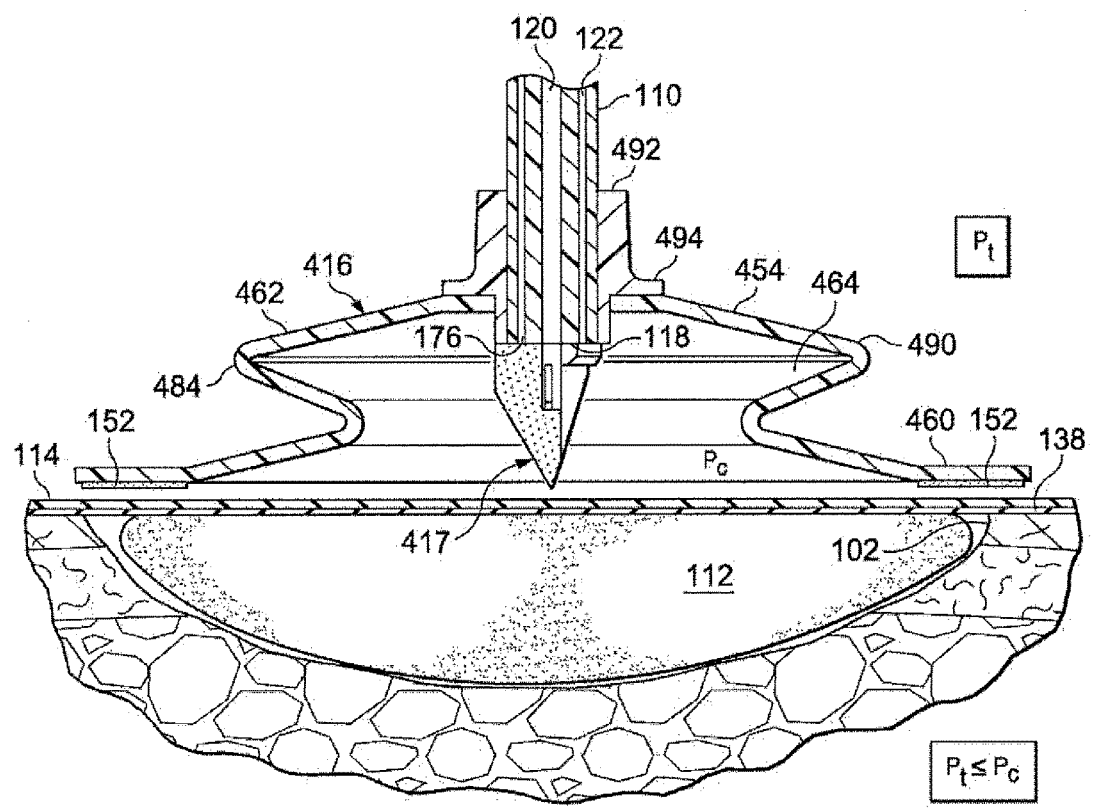
FIG. 9A is a schematic, cross-sectional view of the reduced-pressure interface of FIG. 8 being applied on a patient, but prior to reduced pressure being supplied.
Figure 9B:
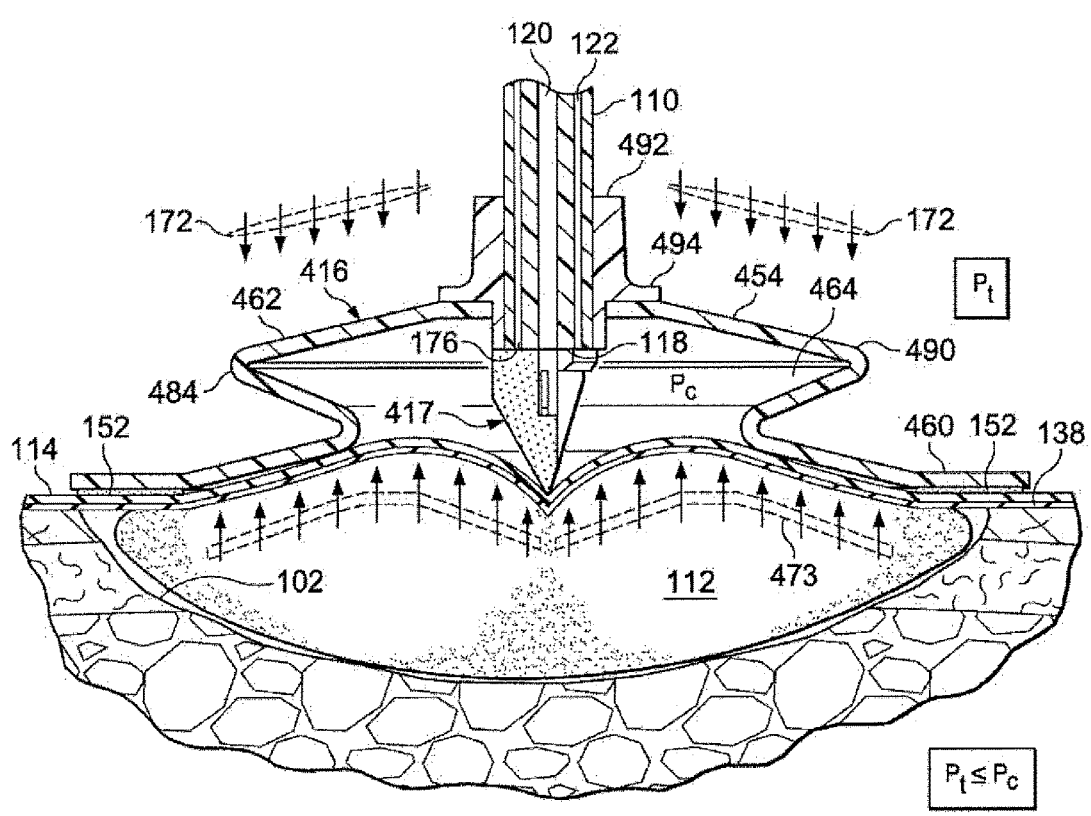
FIG. 9B is a schematic, cross-sectional view of the reduced-pressure interface of FIG. 8 under reduced pressure prior to the cutting element perforating a sealing member.
Figure 9C:
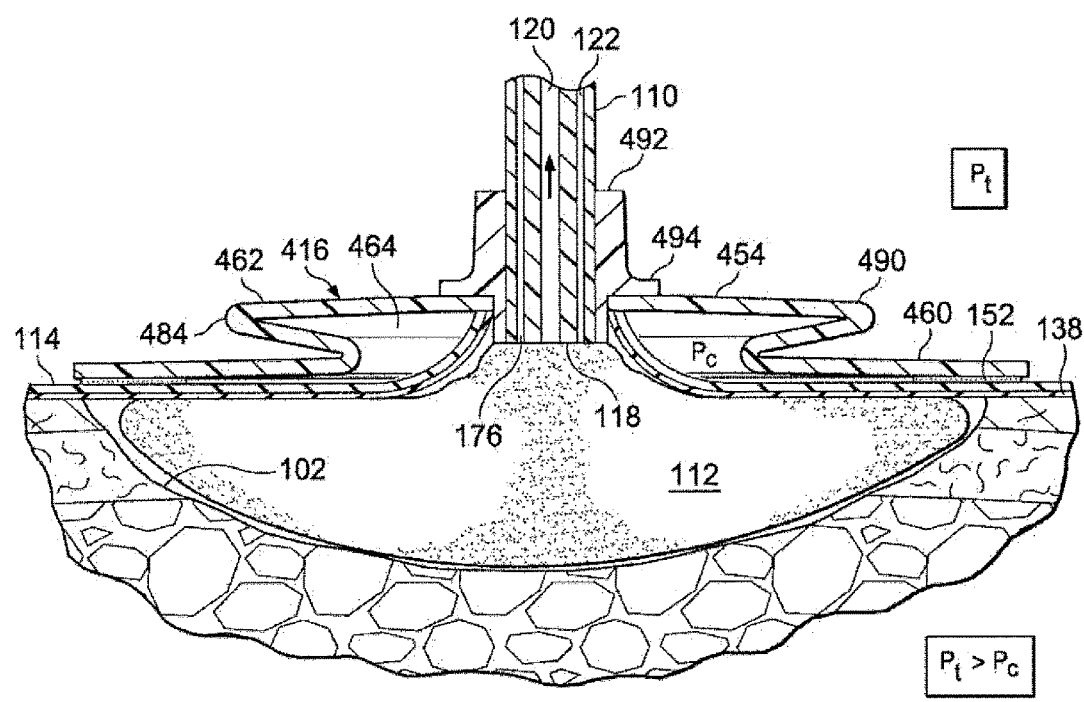
FIG. 9C is a schematic, cross-sectional view of the reduced-pressure interface of FIG. 8 under reduced pressure after the cutting member has perforated the sealing member and the cutting element has been removed.

Referring now primarily to FIGS. 8-9C, another illustrative embodiment of a reduced-pressure interface 416 is presented. The reduced-pressure interface 416 is analogous in many respects to the reduced-pressure interface 316 of FIGS. 5A and 5B. The reduced-pressure interface 416 includes a housing 454 and a cutting element 417. The housing 454 may have a flange portion 460 and a cavity wall portion 462. The flange portion 460 may be coupled to the sealing member 114 by the attachment device 152. The cavity wall portion 462 is collapsible under reduced pressure. The cavity wall portion 462 may include a bellows configuration 490 for permitting the cavity wall portion 462 to collapse when a cavity pressure ($P_c$) inside a cavity 464 is less than a threshold pressure ($P_t$) on an absolute pressure side.

The reduced-pressure interface 416 may further include a conduit adapter 492 for receiving the multi-lumen conduit 110 to provide fluid communication between the reduced-pressure treatment unit 108 and the tissue site 102. The conduit adapter 492 includes an adapter flange 494. The adapter flange 494 is positioned on an exterior 484 of the cavity wall portion 462. In a specific, non-limiting example, the conduit adapter 492 and the adapter flange 494 may be formed from materials to include plasticized polyvinyl chloride (PVC), polyurethane, cyclic olefin copolymer elastomer, thermoplastic elastomer, poly acrylic, silicone polymer, and polyether block amide copolymer.

The multi-lumen conduit 110 is connected to the conduit adapter 492. In a specific, non-limiting embodiment, the multi-lumen conduit 110 may be connected to the conduit adapter 492 by a weld or an adhesive. The multi-lumen conduit 110 extends beyond the conduit adapter 492 into the cavity 464. The reduced-pressure interface 416 is configured to position the distal end 118 of the multi-lumen conduit 110 in contact with the distribution manifold 112.

The cutting element 417 may be at least temporarily coupled to the conduit adapter 492. The cutting element 417 is configured to make orthogonal cuts in the sealing member 114 when the housing 454 is compressed with the driving force 172 thereby impacting the cutting element 417. The cutting element 417 is thus driven into the sealing member 114. The driving force 172 may be manually applied to the exterior 484 of the reduced-pressure interface 416 causing the housing 454 to collapse and thereby driving or pushing the cutting element 417 into the sealing member 114. In another embodiment, the driving force 172 is applied by applying reduced pressure to the cavity 464 such that the cavity pressure ($P_c$) in the cavity 464 is less than a threshold pressure ($P_t$). When the cavity pressure ($P_c$) in the cavity 464 is less than the threshold pressure ($P_t$), the cavity wall portion 462 collapses and impacts the cutting element 417. With continued reduced pressure, a portion of the cutting element 417 is driven through the sealing member 114. The threshold pressure ($P_t$) is at least in part dependent on the type and thickness of material used for the housing 454. In the event reduced pressure is applied to the cavity 464, a tensile force 473 may be applied to the sealing member 114 causing the sealing member 114 to be pulled into the cavity 464. This movement helps the cutting element 417 to be driven into the sealing member 114.

In one embodiment, the cutting element 417 may be formed from a liquid soluble material such as a water soluble material adapted to allow the cutting element 417 to dissolve. The water soluble material may include at least one of the following: Polyvinyl alcohol (PVOH), polyvinyl pyrrolidone, hydroxyl and carboxyl modified cellulose, hydroxyl and carboxyl modified acrylics, starch, sugars (sucrose, glucose, fructose), weak acids (tartaric, citric, malic), salts (sodium chloride, sodium carbonate, sodium bicarbonate), polyethylene oxide (PEO), polyethylene glycol (PEG). The cutting element 417 may dissolve as liquids are removed from the tissue site 102. Reduced pressure is applied to the reduced-pressure interface 416 typically causing liquids to be removed from the tissue site 102. After a sufficient amount of time, liquids removed from the tissue site 102 may cause the cutting element 417 to substantially dissolve. As the cutting element 417 is dissolved, the cutting element 417 is removed by the multi-lumen conduit 110 with the liquids from the tissue site 102. While the cutting element 417 may be dissolvable, it is worth noting that the conduit adapter 492 and the adapter flange 494 do not dissolve.

Once the cutting element 417 has substantially dissolved, reduced pressure applied through the reduced-pressure interface 416 may be of sufficient reduced pressure in the cavity 464 to pull a portion of the distribution manifold 112 into the cavity 464 and into contact with the primary lumen 120 of the multi-lumen conduit 110. The distribution manifold 112 abuts the distal end 118 of the multi-lumen conduit 110 including the distal aperture 176 of the at least one of the plurality of sensing lumens 122. Allowing the distribution manifold 112 to completely abut the distal end 118 of the multi-lumen conduit 110 may help ensure fluid isolation between each of the lumens in the multi-lumen conduit 110.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems. It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site, comprising:
    a distribution manifold for placing proximate to the tissue site;
    a sealing member for covering the distribution manifold;
    a reduced-pressure interface for coupling to the sealing member and comprising a housing forming a cavity adapted to collapse;
    a reduced-pressure source; and
    a multi-lumen conduit comprising at least one sensing lumen configured to be drawn into contact with the distribution manifold.

2. The system of claim 1, wherein the multi-lumen conduit further comprises a primary lumen for delivering reduced pressure, and wherein the primary lumen comprises a central lumen and the at least one sensing lumen comprises a peripheral lumen.

3. The system of claim 2, wherein a distal end of the primary lumen and a distal end of the at least one sensing lumen contact the distribution manifold.

4. The system of claim 1, wherein the cavity of the reduced-pressure interface is fluidly coupled to the distribution manifold through an aperture in the sealing member.

5. The system of claim 1, wherein the housing is adapted to collapse when exposed to a pressure ($P_c$) in the cavity that is less than a threshold pressure ($P_t$).

6. The system of claim 1, further comprising an instrumentation unit fluidly coupled to the at least one sensing lumen, wherein the instrumentation unit includes a pressure sensor and a microprocessor, wherein the microprocessor is configured to process a pressure signal from the pressure sensor.

7. The system of claim 1, wherein the reduced-pressure interface further comprises:
    a cutting element at least temporarily coupled to the housing proximate to a tissue-facing opening, the cutting element adapted to form an aperture in the sealing member if the housing collapses.

8. The system of claim 7, wherein the cutting element is formed from a water soluble material.

9. The system of claim 7, wherein the distribution manifold has a thickness greater than T when under the influence of reduced pressure at an operating level, wherein the cutting element has a piercing length ($L_p$), wherein $L_p<T$, and wherein the cutting element creates an aperture in the distribution manifold.

10. A method for treating a tissue site, comprising:
    disposing a distribution manifold proximate to the tissue site;
    covering the distribution manifold with a sealing member to form a sealed space in which the distribution manifold is disposed;
    coupling a reduced-pressure interface to the sealing member, wherein the reduced-pressure interface comprises a semi-rigid material forming a cavity adapted to collapse;
    fluidly coupling a first conduit and a second conduit to the cavity;
    collapsing the cavity to dispose an end of the second conduit in contact with the distribution manifold; and
    delivering reduced pressure through the first conduit to the cavity.

11. The method of claim 10, further comprising monitoring levels of the reduced pressure through the second conduit.

12. The method of claim 10, wherein collapsing the cavity comprises applying reduced pressure through the reduced-pressure interface to pull a portion of the distribution manifold into the cavity such that the distribution manifold contacts the second conduit.

13. The method of claim 10, wherein collapsing the cavity comprises manually applying a driving force to an exterior of the reduced-pressure interface.

14. The method of claim 10, wherein the semi-rigid material is adapted to collapse when under reduced pressure less than a threshold pressure ($P_t$).

15. The method of claim 10, wherein fluidly coupling the first conduit and the second conduit to the cavity comprises:
    driving a cutting member through the sealing member to create an aperture in the sealing member; and
    dissolving the cutting member causing the second conduit to contact the distribution manifold through the aperture in the sealing member.

* * * * *